US012600945B2

(12) United States Patent
Yin et al.

(10) Patent No.: US 12,600,945 B2
(45) Date of Patent: Apr. 14, 2026

(54) HUMAN Vγ9Vδ2T CELL PROLIFERATION CULTURE METHOD AND CULTURE MEDIUM

(71) Applicant: GUANGDONG GD KONGMING BIOTECH LLC, Guangdong (CN)

(72) Inventors: Zhinan Yin, Guangdong (CN); Yangzhe Wu, Guangdong (CN); Yan Xu, Guangdong (CN)

(73) Assignee: GUANGDONG GD KONGMING BIOTECH LLC, Guangdong (CN)

( * ) Notice: Subject to any disclaimer, the term of this patent is extended or adjusted under 35 U.S.C. 154(b) by 1265 days.

(21) Appl. No.: 17/418,103

(22) PCT Filed: Feb. 19, 2019

(86) PCT No.: PCT/CN2019/075491
§ 371 (c)(1),
(2) Date: Jun. 24, 2021

(87) PCT Pub. No.: WO2020/133643
PCT Pub. Date: Jul. 2, 2020

(65) Prior Publication Data
US 2021/0332328 A1      Oct. 28, 2021

(30) Foreign Application Priority Data
Dec. 24, 2018    (CN) .......................... 201811580040.2

(51) Int. Cl.
*C12N 5/0783* (2010.01)
*A61K 35/17* (2025.01)
*A61K 40/11* (2025.01)
*A61K 40/42* (2025.01)
*A61P 35/00* (2006.01)

(52) U.S. Cl.
CPC ........... *C12N 5/0636* (2013.01); *A61K 40/11* (2025.01); *A61K 40/42* (2025.01); *A61P 35/00* (2018.01); *A61K 2239/31* (2023.05); *A61K 2239/38* (2023.05); *A61K 2239/55* (2023.05); *C12N 2500/38* (2013.01); *C12N 2501/2302* (2013.01); *C12N 2501/2315* (2013.01)

(58) Field of Classification Search
CPC .............. C12N 5/0636; C12N 2500/38; C12N 2501/2302; C12N 2501/2315; A61K 40/11
See application file for complete search history.

(56) References Cited

U.S. PATENT DOCUMENTS

2018/0298337 A1* 10/2018 Kaneko ................ C12N 5/0637

FOREIGN PATENT DOCUMENTS

| | | | | |
|---|---|---|---|---|
| CN | 102925411 | A | 2/2013 | |
| CN | 104711224 | A | 6/2015 | |
| CN | 104818248 | A | 8/2015 | |
| CN | 106399242 | A * | 2/2017 | ............ C12N 15/86 |
| CN | 108642006 | A | 10/2018 | |
| CN | 109337870 | A | 2/2019 | |
| CN | 109593712 | A | 4/2019 | |
| EP | 3822342 | A1 | 5/2021 | |
| JP | 2010-017134 | A | 1/2010 | |
| WO | 2009/037723 | A1 | 3/2009 | |
| WO | 2012/009422 | A1 | 1/2012 | |
| WO | 2016/093350 | A1 | 6/2016 | |
| WO | 2018/024896 | A1 | 2/2018 | |
| WO | 2018/195175 | A1 | 10/2018 | |

OTHER PUBLICATIONS

Cornish, G.H., Sinclair, L.V. and Cantrell, D.A., 2006. Differential regulation of T-cell growth by IL-2 and IL-15. Blood, 108(2), pp. 600-608. (Year: 2006).*
Manning, J., Mitchell, B., Appadurai, D.A., Shakya, A., Pierce, L.J., Wang, H., Nganga, V., Swanson, P.C., May, J.M., Tantin, D. and Spangrude, G.J., 2013. Vitamin C promotes maturation of T-cells. Antioxidants & redox signaling, 19(17), pp. 2054-2067. (Year: 2013).*
Dimova, T., Brouwer, M., Gosselin, F., Tassignon, J., Leo, O., Donner, C., Marchant, A. and Vermijlen, D., 2015. Effector Vγ9Vδ2 T cells dominate the human fetal γδ T-cell repertoire. Proceedings of the National Academy of Sciences, 112(6), pp. E556-E565. (Year: 2015).*
Mielnik, P., et al., 2012. Serum concentration of interleukin 15, interleukin 2 receptor and TNF receptor in patients with polymyositis and dermatomyositis: correlation to disease activity. Rheumatology international, 32, pp. 639-643. (Year: 2012).*
Naidu, K.A., 2003. Vitamin C in human health and disease is still a mystery? An overview. Nutrition journal, 2, pp. 1-10. (Year: 2003).*
Manning et al. (2013. Vitamin C promotes maturation of T-cells. Antioxidants & redox signaling, 19(17), pp. 2054-2067 (Year: 2013).*
Cornish et al. (Regulation of T-cell growth by IL-2 and IL-15. Blood, 108(2), pp. 600-608, 2006 (Year: 2006).*

(Continued)

*Primary Examiner* — Jeremy C Flinders
*Assistant Examiner* — Masudur Rahman
(74) *Attorney, Agent, or Firm* — IP & T GROUP LLP

(57) ABSTRACT

A human Vγ9Vδ2T cell proliferation method and a culture medium. The method comprises: first stimulating a human Vγ9Vδ2T cell with a culture medium containing interleukin-2 and phosphonic acid compounds, and then culturing the human Vγ9Vδ2T cell with a culture medium added with interleukin-15 and vitamin C to achieve proliferation culture. The culture medium additionally comprises interleukin-15 and vitamin C. Compared with a conventional proliferation method and a conventional culture medium, the method and the culture medium can improve the proliferation efficiency and cell purity of the human Vγ9Vδ2T cell. The human Vγ9Vδ2T cell obtained by culture in the method has stronger anti-apoptotic ability and longer cell survival time, and moreover, the expression level of critical killer molecules NKG2D thereof is higher, thereby having stronger killing ability to tumor cells.

10 Claims, 5 Drawing Sheets

(56)          References Cited

OTHER PUBLICATIONS

Ma, J et al., Non-Official translation: Contrast of the Percentage and Differentiation Subtypes of Vγ9Vδ2 T Cells in Peripheral Blood before and after Amplification between Patients with Liver Cancer and Healthy People, Contemporary Medicine, Mar. 2016, vol. 22, No. 7.

Li, X et al., Ex Vivo Expansion of Highly Purified NK Cells from Human Peripheral Blood, Journal of Experimental Hematology, Dec. 2007, vol. 15, No. 2, pp. 373-377.

Notification to Grant Patent Right for Invention of priority document application No. CN 201811580040.2 on Jun. 5, 2020.

First Office Action issued for priority document application No. CN 201811580040.2 on Feb. 6, 2020.

First search of priority document application No. CN 201811580040.2 filed on Dec. 24, 2018.

Supplementary search of priority document application No. CN 201811580040.2 filed on Dec. 24, 2018.

Anke J. et al., Peripheral blood monocytes are responsible for γδ T cell activation induced by zoledronic acid through accumulation of IPP/DMAPP, British Journal of Haematology, 2008, pp. 245-250, vol. 144, Blackwell Publishing Ltd.

Jared Manning et al., Vitamin C Promotes Maturation of T-Cells, Antioxidants & Redox Signaling, Dec. 10, 2013, pp. 2054-2067, vol. 19, No. 17.

Supplementary search report of European Patent application No. 19905880.1 issued by the European Patent Office on Feb. 23, 2022.

Office Action for European Patent Application No. 19905880.1 issued by the European Patent Office on Mar. 7, 2022.

Notice of Allowance (=Notification to Grant Patent Right for Invention) for Japanese Patent Application No. 2021-536329 issued by the Japanese Patent Office on May 9, 2023.

* cited by examiner

HUMAN Vγ9Vδ2T CELL PROLIFERATION CULTURE METHOD AND CULTURE MEDIUM

CROSS-REFERENCE TO RELATED APPLICATIONS

This application is a national stage application of PCT/CN2019/075491 filed on Feb. 19, 2019, which claims priority to Chinese Patent Application No. 201811580040.2 filed with the Chinese Patent Office on Dec. 24, 2018, entitled "Human Vγ9Vδ2T Cell Proliferation Method and Culture Medium", which is incorporated herein by reference in its entirety.

TECHNICAL FIELD

The present disclosure relates to the technical field of cell culture, in particular, to a human Vγ9Vδ2T cell proliferation method and a culture medium.

BACKGROUND ART

Immunocyte therapy has become a novel important medical method for treating refractory diseases (such as malignant tumor) in the medical field all around the world, for example, a CAR-T cell is used to treat B-cell lymphoma. For the scientific and medical communities, it is very critical to obtain an immunocyte with stable and reliable quality and good functions for rendering good clinical treatment effect.

Human Vγ9Vδ2T cell which only exists in primates and human beings is a T-cell subset with anti-tumor and anti-infection functions. Human Vγ9Vδ2T cell can be used for immunocyte therapy or immunologic function reconstruction of people who suffers from tumor, refractory infectious diseases or immune function unbalanced diseases.

Currently, there are mainly two types of human Vγ9Vδ2T cell proliferation methods:

the first type of existing proliferation technology is to add the monoclonal antibodies of IL-2 and TCR in the culture medium of peripheral blood mononuclear cells (PBMCs). The main disadvantage of the method is that the two types of γδ T cells (Vδ1 cell subset and Vδ2 cell subset) in the peripheral blood are both proliferated, while the Vδ1 cell subset has an immunosuppressive function, and thus it cannot be applied to immunocyte therapy; and the second type of existing proliferation technology is to add IL-2 and a phosphate small molecule compound such as zoledronic acid in the culture medium of PBMCs. The method can render γδ T cells of the Vδ2 cell subset of a relatively high purity, and thus can be used in immunocyte therapy, and this is a conventional method currently used for proliferating human Vγ9Vδ2T cells in human peripheral blood at home and abroad. However, the method has the following disadvantages: the period of cell culture proliferation is about 14 days, the proliferated human Vγ9Vδ2T cells have a relatively short survival time (which can continuously survive for about 7 days), and thus the cell anti-apoptosis ability is not strong, and thus the ability to kill tumor cells is not strong, either.

SUMMARY

The purpose of the present disclosure comprises, for example, providing a human Vγ9Vδ2T cell proliferation method, which can improve the proliferation efficiency and the cell purity of human Vγ9Vδ2T cells, and the cultured human Vγ9Vδ2T cells have relatively stronger killing ability and suppressive ability to tumor, and have a stronger anti-apoptotic ability and a longer cell survival time.

The purpose of the present disclosure also comprises, for example, providing a human Vγ9Vδ2T cell culture medium, and the culture medium is used to culture the human Vγ9Vδ2T cells and can improve the proliferation efficiency and the cell purity of the human Vγ9Vδ2T cells, and the cultured human Vγ9Vδ2T cells have a relatively stronger killing ability and suppressive ability to tumor, and have a stronger anti-apoptotic ability and a longer cell survival time.

The purpose of the present disclosure also comprises, for example, providing a human Vγ9Vδ2T cell stimulation and proliferation culture medium, which can selectively proliferate the human Vγ9Vδ2T cells from the peripheral blood mononuclear cells, and the proliferated human Vγ9Vδ2T cells have high purity, stronger killing ability and stronger anti-apoptotic ability.

The present disclosure provides a T cells proliferation method, comprising:

step A, culturing a composition containing the T cells, by using a first culture medium which is able to stimulate the T cells, to stimulate the T cell; and step B, using a second culture medium to culture the stimulated T cells; wherein the second culture medium contains interleukin-2, interleukin-15, and vitamin C or derivatives of vitamin C.

In one or multiple embodiments, the T cells comprises Vγ9Vδ2T cells.

In one or multiple embodiments, the first culture medium comprises interleukin-2 and phosphonic acid compounds.

In one or multiple embodiments, the first culture medium comprises interleukin-2, phosphonic acid compounds, interleukin-15, and vitamin C or derivatives of vitamin C.

In one or multiple embodiments, the derivatives of vitamin C are selected from vitamin C ethyl ether, vitamin C palmitate, vitamin C glucoside, vitamin C magnesium phosphate and vitamin C sodium phosphate.

In one or multiple embodiments, in the second culture medium, the concentration of the interleukin-15 is 1-1000 ng/ml.

In one or multiple embodiments, in the second culture medium, the concentration of the vitamin C or derivatives of vitamin C is 10 μM-800 mM.

In one or multiple embodiments, in the second culture medium, the concentration of the interleukin-2 is 1-1000 ng/ml.

In one or multiple embodiments, the composition containing the T cells comprises peripheral blood mononuclear cells extracted from the peripheral blood of a human body.

In one or multiple embodiments, in step A, the culture duration is 60-100 hours.

In one or multiple embodiments, the phosphonic acid compounds comprise bisphosphoric acid compounds, preferably, selected from the group consisting of zoledronic acid, etidronic acid, ibandronic acid, pamidronic acid, alendronic acid, risedronic acid, minodronic acid and combinations thereof, for example, zoledronic acid.

In one or multiple embodiments, the second culture medium comprises a basic culture medium, interleukin-2, interleukin-15, and vitamin C or derivatives of vitamin C.

In one or multiple embodiments, the basic culture medium is selected from the group consisting of RPMI-1640 culture medium, D-MEM, MEM, RPMI, Opti-MEM and combinations thereof, for example, RPMI-1640 culture medium.

The present disclosure also provides a culture medium, comprising a basic culture medium, interleukin-2, interleukin-15, and vitamin C or derivatives of vitamin C.

In one or multiple embodiments, the concentration of the interleukin-2 in the culture medium is 1-1000 ng/ml, the concentration of the interleukin-15 is 1-1000 ng/ml, and the concentration of the vitamin C or derivatives of vitamin C is 10 μM-800 mM.

The present disclosure also provides a pharmaceutical composition, comprising the T cells obtained by using the proliferation method according to the present text and a pharmaceutically acceptable carrier.

The present disclosure also provides a pharmaceutical composition, comprising the Vγ9Vδ2T cells obtained by using the proliferation method according to the present text and a pharmaceutically acceptable carrier.

In one or multiple embodiments, the pharmaceutical composition is a cell suspension.

The present disclosure also provides use of the T cells obtained by the proliferation method according to the present disclosure or the pharmaceutical composition of the present disclosure in preparation of medicines for suppressing, preventing or treating infectious diseases, autoimmune diseases or malignant diseases.

In one or multiple embodiments, the malignant disease is cancer.

In one or multiple embodiments, the malignant disease is lung cancer.

The present disclosure also provides a method for suppressing, preventing or treating infectious diseases, autoimmune diseases or malignant diseases, comprising:

(1) extracting peripheral blood mononuclear cells from the peripheral blood of a subject in need;

(2) proliferating the peripheral blood mononuclear cells through the proliferation method of the present disclosure; and (3) administering the proliferated product to the subject in need.

The present disclosure also provides the use of the T cells obtained by the proliferation method according to the present text or the pharmaceutical composition of the present text in suppressing, preventing or treating infectious diseases, autoimmune diseases or malignant diseases.

The present disclosure also provides the use of the culture medium of the present text used for proliferating T cells.

In one or multiple embodiments, the T cells are Vγ9Vδ2T cells.

The present disclosure provides a human Vγ9Vδ2T cell proliferation method, comprising:

step 1, extracting peripheral blood mononuclear cells from the peripheral blood of a human body;

step 2, providing a first culture medium, resuspending the peripheral blood mononuclear cells by using the first culture medium, to obtain a cell suspension, wherein the first culture medium comprises a second culture medium and phosphonic acid compounds; and the second culture medium comprises a basic culture medium, and interleukin-2, interleukin-15, and vitamin C or derivatives of vitamin C added in the basic culture medium; and the order of the step 1 and the step 2 can be adjusted;

step 3 (or step A), inoculating the cell suspension into a cell culture container to culture for 60-100 hours; and step 4 (or step B), using the second culture medium to change the medium, wherein the second culture medium is used in all the subsequent culture processes.

In one or multiple embodiments, the basic culture medium is the RPMI-1640 culture medium; and the phosphonic acid compounds comprise one or a plurality of zoledronic acid, etidronic acid, ibandronic acid, pamidronic acid, alendronic acid, risedronic acid, minodronic acid.

In one or multiple embodiments, in step 2, the cell density of the cell suspension is $3\sim4\times10^6$ cells/ml.

In one or multiple embodiments, in step 2, in the first culture medium, the concentration of the phosphonic acid compounds is 1-1000 μM; and In the first culture medium and the second culture medium, the concentration of the interleukin-2 is 1-1000 ng/ml, the concentration of the interleukin-15 is 1-1000 ng/ml, and the concentration of the vitamin C or derivatives of vitamin C is 10 μM-800 mM.

In one or multiple embodiments, the cell culture container is a 24-well plate, 48-well plate or 96-well plate; in the step 3, the cell suspension is inoculated into the cell culture container to culture for 72 hours; and in the subsequent culture process in the step 4, the medium for cells is changed every 48-72 hours.

The present disclosure also provides a culture medium, comprising a basic culture medium, and interleukin-2, interleukin-15, and vitamin C added in the basic culture medium.

In one or multiple embodiments, the basic culture medium is the RPMI-1640 culture medium.

In one or multiple embodiments, in the culture medium, the concentration of the interleukin-2 is 1-1000 ng/ml, the concentration of the interleukin-15 is 1-1000 ng/ml, and the concentration of the vitamin C is 10 μM-800 mM.

The present disclosure also provides a first culture medium, which comprises a second culture medium and phosphonic acid compounds.

In one or multiple embodiments, in the first culture medium, the concentration of the phosphonic acid compounds is 1-1000 μM.

The present disclosure has the following advantageous effects:

(1) compared with a conventional proliferation method (the second type of proliferation technology), the human Vγ9Vδ2T cells obtained by the proliferation method of the present disclosure has a higher proliferation efficiency and a higher cell purity; 90% cell purity can be reached when culturing is conducted for 10-12 days (starting from step 3), and the cell proliferation ratio reaches more than 1000 times (i.e., it can proliferate 100,000 human Vγ9Vδ2T cells to at least 100 million human Vγ9Vδ2T cells), which obviously shortens the proliferation culture period of the human Vγ9Vδ2T cells;

(2) compared with the human Vγ9Vδ2T cells obtained by the conventional proliferation method (the second type of proliferating technology), the human Vγ9Vδ2T cells obtained by the proliferation method of the present disclosure have stronger killing and suppressing abilities to tumor; and (3) the human Vγ9Vδ2T cells obtained by the proliferation method of the present disclosure have a stronger anti-apoptotic ability and a longer survival time, and after the cell proliferation culture period (10-12 days starting from step 3) ends, the human Vγ9Vδ2T cells obtained by the proliferation method of the present disclosure can continue to survive about 20 days.

BRIEF DESCRIPTION OF THE DRAWINGS

In order to more clearly illustrate technical solutions of embodiments of the present disclosure, accompanying drawings which need to be used in the embodiments will be introduced briefly below, and it should be understood that the accompanying drawings below merely show some embodiments of the present disclosure, therefore, they should not be considered as limitation to the scope.

DETAILED DESCRIPTION OF THE EMBODIMENTS

Terms Used by the Present Disclosure

Figure 1:
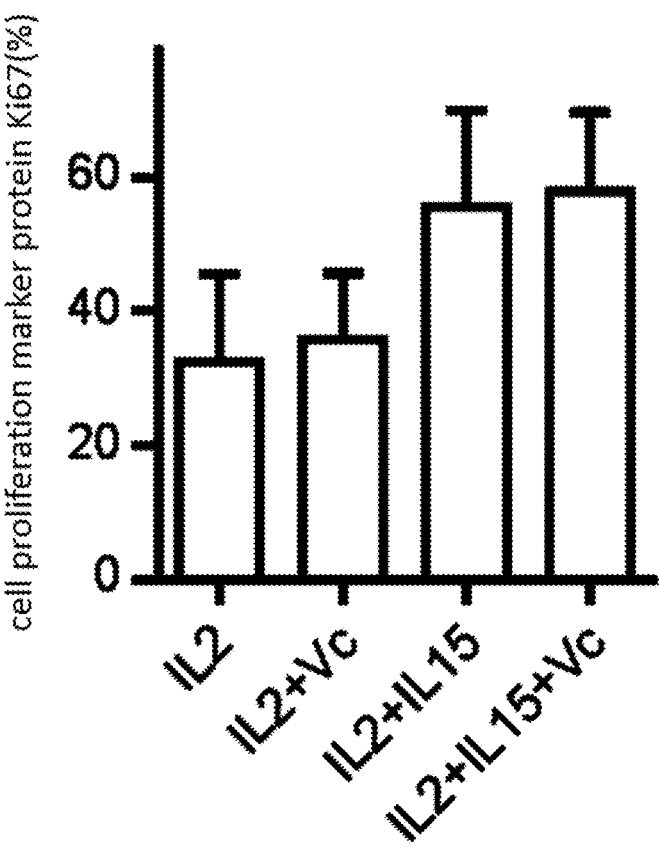
FIG. 1 is a comparison chart of the proliferation efficiencies when four different culture mediums are used to conduct proliferation culture to the human Vγ9Vδ2T cells.

The term of "basic culture medium" used in the present text refers to a solution containing nutrients that nourish the growth of mammalian cells. The basic culture medium provides standard inorganic salts such as zinc, iron, magnesium, calcium and potassium, and vitamins, glucose, buffer system and essential amino acids. For example, the basic culture medium is RPMI-1640 culture medium, D-MEM, MEM, RPMI, Opti-MEM or the combinations thereof.

The term of "prepared by" has the same meaning with "containing". The terms of "include", "comprise", "have", "contain" or any other variants used herein are intended to cover non-exclusive comprising. For example, the composition, step, method, article or device comprising listed elements is not necessary to be limited to those elements, other elements not explicitly listed or elements inherent in such a composition, step, method, article or device can also be contained.

The conjunction phrase of "consist of" excludes any unspecified elements, steps or components. If used in a claim, this phrase will make the claim closed, so that the claim does not comprise materials other than those described, except for the conventional impurities associated with them. When the phrase of "consist of" appears in a sub-sentence of the subject of the claim rather than immediately after the subject, it only defines the elements described in the sub-sentence; and other elements are not excluded from the claim as an entirety.

When the amount, concentration, or other value or parameter is expressed by a range, a preferred range, or a range defined by a series of preferred upper limit values and preferred lower limit values, it should be understood as the discourse of all ranges formed by any pairing of any upper limit or preferred value of any range and any lower limit or preferred value of any range, regardless of whether the range is separately disclosed. For example, when the range of "1~5" is disclosed, the described range should be explained to comprise the ranges of "1~4", "1~3", "1~2", "1~2 and 4~5", "1~3 and 5" and the like. When the value range is described in the present text, unless otherwise described, the range intends to comprise its end values and all integers and fractions within the range.

The term of "parts by mass" refers to the basic unit of measurement that represents the mass ratio relationship of multiple components; 1 part can represent any unit mass, for example, it can represent 1 g, or 2.689 g and the like. If the parts by mass of component A is a parts and the parts by mass of component B is b parts, then it shows that the mass ratio of component A to component B is a:b. Or, it shows that the mass of the component A is aK, and the mass of the component B is bK (K is a random number, representing the multiple factor). What should not be misunderstood is that the sum of the parts by mass of all the components is not limited to 100 parts, which is different from the mass fraction.

The term of "and/or" is used to refer that one or both of the described conditions may occur, for example, A and/or B comprises (A and B) and (A or B).

In addition, the indefinite articles "a" and "an" before an element or component of the present disclosure have no restriction on the quantity (i.e., the occurrence times) of the element or component. Therefore, "a" and "an" should be understood to comprise one or at least one, and the element or component in the singular form also contains the plural form, unless the number described is clearly intended to refer to the singular form.

The term of "derivatives of vitamin C" generally is a type of compounds with an enediol structure that stabilizes a reduced vitamin C by introducing other groups to the carbon atom at position 2 of vitamin C. Examples of derivatives of vitamin C comprise vitamin C phosphate, such as vitamin C magnesium phosphate and vitamin C sodium phosphate; vitamin C palmitate, and vitamin C ethyl ether; and vitamin C carbohydrates, such as vitamin C glucoside and the like.

The terms of "peripheral blood mononuclear cells", "PBMCs" or "mononuclear cell" refer to mononuclear cells separated from the peripheral blood, and are usually used for anti-cancer immunotherapy. The peripheral blood mononuclear cells can be obtained from collected human blood using, for example, Ficoll-Hypaque density gradient method.

The "peripheral blood mononuclear cells" can be obtained from normal people, subjects who are at risk of having disease, or patients. The peripheral blood mononuclear cells used here need not necessarily be derived from the autologous, and allogeneic peripheral blood mononuclear cells can also be used.

The term of "malignant disease" in the present text is used in the broadest sense thereof, and refers to diseases characterized by uncontrolled cell growth. It comprises, but is not limited to, adrenocortical carcinoma, anal cancer, bladder cancer, ependymoma, medulloblastoma, breast cancer, cervical cancer, colon cancer, endometrial cancer, esophageal cancer, extrahepatic cholangiocarcinoma, eye cancer, gallbladder cancer, gastric cancer, germ cell tumors, extragonadal cancer, head and neck cancer, hypopharyngeal cancer, pancreatic islet cell cancer, laryngeal cancer, leukemia, acute lymphoblastic leukemia, oral cancer, liver cancer, lung cancer, and the like.

The term of "autoimmune disease" refers to diseases and disorders caused by the body's immune response to its own tissues, which causes prolonged inflammation and subsequent tissue destruction. Examples of autoimmune diseases comprise, but is not limited to, alopecia areata, type 1 diabetes, Guillain-Barré syndrome, multiple sclerosis, rheumatoid arthritis, scleroderma, polymyositis, vitiligo, and systemic lupus erythematosus.

The term of "infectious disease" can be the result of any pathogen. Its examples comprise, but is not limited to, the result of viral infections such as AIDS, hepatitis B and C, cell infections, bacterial infections, parasites and fungal infections.

The present disclosure firstly provides a human Vγ9Vδ2T cell proliferation method, comprising:

step 1, extracting peripheral blood mononuclear cells (PBMC) from the peripheral blood of a human body;

step 2, providing a first culture medium, resuspending the peripheral blood mononuclear cells by using the first culture medium, to obtain cell suspension, wherein the first culture medium comprises a second culture medium and phosphonic acid compounds; and the second culture medium comprises a basic culture medium, and interleukin-2 (IL-2), interleukin-15 (IL-15), and vitamin C added in the basic culture medium; and the order of the step 1 and the step 2 can be adjusted;

step 3, inoculating the cell suspension into the cell culture container to culture for 60-100 hours; and step 4, using the second culture medium to change the medium, and using the second culture medium in all the subsequent culture processes.

Specifically, in the step 1, the basic culture medium is RPMI-1640 culture medium. RPMI is short for Roswell Park Memorial Institute, representing Roswell Park Memorial Institute. RPMI is a type of cell culture medium developed by the institute, and 1640 refers to the code name of the culture medium. 10% fetal bovine serum is added when using this culture medium.

Optionally, the phosphonic acid compounds comprise one of or a plurality of zoledronic acid (zoledronate, ZOL), etidronic acid, ibandronic acid, pamidronic acid, alendronic acid, risedronic acid, minodronic acid.

In an embodiment of the present disclosure, the phosphonic acid compound is zoledronic acid.

Specifically, in the step 2, the cell density of the cell suspension is 3~4×10$^6$ cells/ml.

Specifically, the purpose of steps 2 and 3 lies in culturing the peripheral blood mononuclear cells by using the first culture medium which contains phosphonic acid compounds, selectively proliferating human Vγ9Vδ2T cells in the peripheral blood mononuclear cells, and suppressing the growing of other cells to make other cells apoptotic.

Optionally, the cell culture container is a 24-well plate, 48-well plate or 96-well plate.

The purpose of the step 4 is to further proliferate the human Vγ9Vδ2T cells with a relatively high purity obtained by the selective proliferation in step 3, to further add the amount of human Vγ9Vδ2T cells.

Specifically, in the step 2, in the first culture medium, the concentration of the phosphonic acid compound is 1-100001 μM; and in the first culture medium and the second culture medium, the concentration of the interleukin-2 is 1-1000 ng/ml, the concentration of the interleukin-15 is 1-1000 ng/ml, and the concentration of the vitamin C is 10 μM-800 mM.

Preferably, in the step 3, the cell suspension is inoculated into the cell culture container to culture for 72 hours.

Specifically, in the subsequent culture process in the step 4, the medium for cells is changed every 48-72 hours.

Specifically, the total culture duration of the steps 3 and 4 usually is 10-12 days, and the cells at this point reach a sufficient amount and has the strongest killing ability, which are especially suitable for cell therapy.

The present disclosure provides a T cell proliferation method, comprising:

step A, using a first culture medium that comprises interleukin-2 and phosphonic acid compounds, and optionally also comprises interleukin-15, and vitamin C or derivatives of vitamin C to culture a composition containing the T cells to stimulate the T cells; and step B, using a second culture medium that contains interleukin-2, interleukin-15, and vitamin C or derivatives of vitamin C to culture the stimulated T cells.

The present disclosure provides a human Vγ9Vδ2T cell proliferation method, comprising:

step A, using a culture medium that comprises interleukin-2 and phosphonic acid compounds, and optionally also comprises interleukin-15, and vitamin C or derivatives of vitamin C to culture a composition containing the T cells to stimulate the T cells;

step B, selecting and separating human Vγ9Vδ2T cells from the stimulated peripheral blood mononuclear cells; and step C, using a second culture medium that contains interleukin-2, interleukin-15, and vitamin C or derivatives of vitamin C to culture the selected and separated human Vγ9Vδ2T cells.

The present disclosure provides a human Vγ9Vδ2T cell proliferation method, comprising:

step A, extracting peripheral blood mononuclear cells (PBMC) from peripheral blood;

step B, using a culture medium which can stimulate T cells to culture a composition containing the T cells to stimulate the T cells;

step C, selecting and separating human Vγ9Vδ2T cells from the stimulated peripheral blood mononuclear cells; and step D, using a second culture medium that contains interleukin-2, interleukin-15, and vitamin C or derivatives of vitamin C to culture the selected and separated human Vγ9Vδ2T cells.

The present disclosure provides a method for suppressing, preventing or treating infectious diseases, autoimmune diseases or malignant diseases, comprising:

(1) extracting peripheral blood mononuclear cells from the peripheral blood of a first subject;

(2) using a culture medium that contains interleukin-2 and phosphonic acid compounds, and optionally also contains interleukin-15, and vitamin C or derivatives of vitamin C to culture peripheral blood mononuclear cells to stimulate the human Vγ9Vδ2T cells;

(3) using a second culture medium that contains interleukin-2, interleukin-15, and vitamin C or derivatives of vitamin C to culture the stimulated human Vγ9Vδ2T cells;

(4) administering the cultured cells to a second subject, wherein preferably, the first subject and the second subject can be a same subject. Alternatively, the first subject and the second subject are different subjects.

In the above, the peripheral blood mononuclear cells are compositions containing T cells, and preferably, the malignant disease is cancer, for example, lung cancer.

In the human Vγ9Vδ2T cell proliferation method of the present disclosure, the operating methods without specific conditions are carried out in accordance with the methods described in general conditions (for example, *Short Protocols in Molecular Biology*, edited by F. M. Ausubel, R. E. Kingston, J. G. Seidman, et al, translated by Ma Xuejun, Shu Yuelong, Beijing: Science Press, 2004).

The critical technical feature of the present disclosure is the use of interleukin-15 and vitamin C in the cell culture process, through adding interleukin-15 and vitamin C in the process of proliferation culture of the human Vγ9Vδ2T cells, compared with the conventional proliferation method (the second type of proliferating technology), the proliferation efficiency and cell purity of the human Vγ9Vδ2T cells can be improved, and the cultured human Vγ9Vδ2T cells have stronger anti-apoptotic ability and longer cell survival time; in addition, the expression level of critical killer molecule NKG2D thereof is higher, and then the killing ability to tumor cells is stronger. Compared with the second type of the existing proliferating technology (referring to the introduction in the background art for the details), the present disclosure solves, for example, the technical problems of low proliferation efficiency and low purity, the problem that the obtained cells do not have a strong killing ability, and the technical problems that the obtained cells do not have enough survival time and the obtained cells are prone to senescence and apoptosis, and the like.

To sum up, the human Vγ9Vδ2T cell proliferation method of the present disclosure has the following advantageous effects:

(1) compared with a conventional proliferation method (the second type of proliferation technology), the human Vγ9Vδ2T cells obtained by the proliferation method of the present disclosure have a better proliferation efficiency and a higher cell purity; 90% cell purity can be reached when the culture is conducted for 10-12 days (starting from step 3), and the cell proliferation ratio reaches more than 1000 times (i.e., it can proliferate 100,000 human Vγ9Vδ2T cells to at least 100 million human Vγ9Vδ2T cells), which obviously shortens the period of proliferation culture for the human Vγ9Vδ2T cells;

(2) compared with the human Vγ9Vδ2T cells obtained by the conventional proliferation method (the second type of proliferating technology), the human Vγ9Vδ2T cells obtained by the proliferation method of the present disclosure have stronger killing and suppressing abilities to tumor; and (3) the human Vγ9Vδ2T cells obtained by the proliferation method of the present disclosure have a stronger anti-apoptotic ability and a longer cell survival time, and after the cell proliferation culture period (starting from step 3, for 10-12 days) ends, the human Vγ9Vδ2T cells obtained by the proliferation method of the present disclosure can continue surviving for about 20 days.

Based on the above-mentioned human Vγ9Vδ2T cell proliferation method, the present disclosure also provides a human Vγ9Vδ2T cell culture medium (also referred to as the second culture medium in the present text), which comprises a basic culture medium and interleukin-2, interleukin-15, and vitamin C added in the basic culture medium.

In one or multiple embodiments, the basic culture medium is the RPMI-1640 culture medium.

In one or multiple embodiments, in the first culture medium and the second culture medium, the concentration of the interleukin-2 is 1-1000 ng/ml, 1-500 ng/ml, 1-200 ng/ml, or 70-130 ng/ml. In one or multiple embodiments, in the second culture medium, the concentration of the interleukin-15 is 1-1000 ng/ml, 1-500 ng/ml, 1-200 ng/ml, or 70-130 ng/ml. In one or multiple embodiments, in the second culture medium, the concentration of the of the vitamin C is 10 μM-800 mM, or 20 μM-400 mM, or 50 μM-100 μM.

The present disclosure also provides a human Vγ9Vδ2T cell stimulation and proliferation culture medium (also referred to as the first culture medium in the present text), which comprises the above-mentioned second culture medium and phosphonic acid compounds.

Optionally, in the first culture medium, the concentration of the phosphonic acid compound is 1-1000 μM.

EXAMPLES

Experimental Reagents and Materials

Main reagents and materials used in the experiments were provided in the following Table 1.

TABLE 1

| Main reagents and materials | |
| --- | --- |
| Name of the reagent | Name of the company & producing country |
| DiR dye | Invitrogen, USA |
| CFSE | Sigma, USA |
| DMEM culture medium | Gibco, USA |
| RPMI-1640 culture medium | Gibco, USA |
| Penicillin-streptomycin solution | Gibco, USA |
| PBS | Dongguan Jinan University Research Institute, China |
| Fetal Bovine Serum | Gibco, USA |
| Dimethyl sulfoxide (DMSO) | Sigma, USA |
| Recombinant Human Interleukin 2 Injection | Beijing Sihuan Biopharmaceutical Co., Ltd., China |
| Recombinant human IL-15 | Peprotech, USA |
| L-Ascorbic Acid | Sigma, USA |
| 0.25% Pancreatin | Gibco, USA |
| Zoledronic acid | Sigma, USA |
| Ficoll Lymphocyte Separation Solution | GE Healthcare, USA |
| Red blood cell lysate | Tiangen Biochemical Technology (Beijing) Co., Ltd. |
| Anti-human CD3-BV510 (Clone:SK7) | BD, USA |
| Anti-human TCR Vδ2-PE (Clone:B6) | BD, USA |
| Anti-human CD314 (NKG2D)-PerCP/Cy5.5 (Clone:1D11) | Biolegend, USA |
| Anti-human Ki67-Alexa Fluor ® 647 (Clone: B56) | BD, USA |
| Anti-human CD45RA-PE-cy5 (Clone:HI100) | Biolegend, USA |

TABLE 1-continued

| Main reagents and materials | |
| --- | --- |
| Name of the reagent | Name of the company & producing country |
| Anti-human CD27-Pacific Blue (Clone: O323) | Biolegend, USA |

Example 1: Vγ9Vδ2T Cell Proliferation Effects and Characteristics of Vγ9Vδ2T Cells Obtained by Proliferation Extraction of Peripheral Blood Mononuclear Cells 1) 4 mL of human lymphocyte separation solution was taken and added into a 15 mL conical centrifuge tube, 1×PBS buffer was used to dilute the peripheral blood in equal proportions and mixed thoroughly, and then 10 mL of diluted peripheral blood was slowly spread on the surface of the lymphocyte separation solution along the wall of the test tube, and 600 g centrifuging was conducted for 25 min at 25° C.

2) A sterile Pasteur pipette was used to draw the middle white flocculent cell layer into another sterile centrifuge tube, an equal volume of PBS was added and mixed thoroughly, and then centrifuging was conducted at 1500 rpm for 10 min.

3) After the supernatant was discarded, 5~10 mL red blood cell lysate buffer was added to resuspend the cells to lyse for 3~7 min at room temperature. 5 times of the volume of PBS was added to terminating the lysis. After filtering with a 40 μm screen, centrifuging was conducted at 1500 rpm for 10 min.

4) After the supernatant was discarded, 10 mL of serum-free RPMI1640 culture medium was added to resuspend the cells, and centrifuging was conducted at 1500 rpm for 10 min.

5) After the supernatant was discarded, the RPMI1640 complete culture medium (containing 10% fetal bovine serum) was used to dilute the cells sinking at the bottom of the tube to 2 mL, after mixing thoroughly and slowly, 5 μL of cell diluent was drawn for diluting to an appropriate multiple, and a hemocytometer was used for counting.

Proliferation in Vitro of Vγ9Vδ2T Cell

After the PBMC in fresh blood was separated using the Ficoll separation solution, RPMI-1640 complete culture medium with 10% FBS was used to adjust the cell concentration to 3~4×10⁶ cells/ml, and inoculated to a 24-well plate, and 40 ng/mL IL-2 and 50 μM zoledronic acid were added for stimulating for 3 days. Then, the zoledronic acid was removed, the medium was changed every 2~3 days for passage, and the RPMI-1640 culture medium containing cytokines of the following concentrations was used: 100 IU/mL IL-15, 100 IU/mL IL-2, and 70 μM vitamin C, to culture in a culture incubator at 37° C., 5% $CO_2$, PH=7.2–7.4, and a humidity of 95% for 10-14 days.

Vγ9Vδ2T Cell Purity and Phenotype Identification

Vγ9Vδ2T cells proliferated in vitro for 10~14 days were collected and placed inside a 1.5 mL of EP tube, and then centrifuged at 3500 rpm for 5 min in a miniature centrifuge (Eppendorf 5424), and after the supernatant was discarded, washing was conducted twice with 4° C. pre-cooled PBS; the cells were transferred into the corresponding test tubes according to the blank control tube, isotype control and experimental group, respectively, and each tube contained about 5×10⁵ cells. The control tube and the detection tube were respectively equipped with the following fluorescent antibody staining solution according to the antibody specification: anti-human CD3-V500, anti-human TCR-δ2-PE, anti-human CD45-PE-cy5, anti-human CD27-PB and NKG2D-PE-cy7. The cells were resuspended with the prepared fluorescent antibody staining solution, then placed in a refrigerator at 4° C. or on ice, stained in a dark place for 15-20 minutes, washed twice with PBS, and centrifuged at 3500 rpm for 5 minutes, and the supernatant was discarded, and then the cells were resuspended with 200-300 μL PBS, and the purity and phenotype of Vγ9Vδ2T cells were detected using a flow cytometry.

Vγ9Vδ2T Cell ki67 Assay 1) 7~10×10⁵ Vγ9Vδ2T cells proliferated in vitro for 10~14 days were collected, placed inside a 1.5 mL EP tube, centrifuged at 3500 rpm for 5 min in a miniature centrifuge (Eppendorf 5424), and after discarding the supernatant, washed twice using 4° C. pre-cooled PBS.

2) The cell pellet was resuspended by 100 μL PBS, surface-stained flow cytometry antibody CD3-FITC and TCR-δ2-PE (1:200 dilution) were added, an isotype control antibody of the same color and same concentration was added to the control tube, and they were incubated at 4° C. in the dark for 15 minutes.

3) After staining, the resultant was washed twice in PBS, and centrifuged at 3500 rpm for 5 min.

4) Foxp3 Staining Buffer Set was used to detect the expression level of intra-nuclear ki67 as follows: preparing Fixation & Permeabilization Buffer, evenly mixing F & P Concentration with F & P Diluent in a volume ratio of 1:3; and resuspending the cells with 500 μL F & P Buffer, standing in a refrigerator at 4° C. or on ice in dark place for 0.5-18 hours, thereby fixing and permeabilizing the cells.

5) The 10×Permeabilization Buffer was diluted to 1×Permeabilization Buffer with $ddH_2O$. After fixing, 1 mL 1×Permeabilization Buffer was added, and the resultant was centrifuged at 5500 rpm at 4° C. for 5 min and washed twice.

6) The APC-Ki67 fluorescent antibody was diluted into 1×Perm Buffer in a volume ratio of 1:200 and mixed evenly; the cell pellet was resuspended with a staining solution, placed in a refrigerator at 4° C. or on ice, and stained in dark place for 30 minutes.

7) 1×Perm Buffer solution was added, the resultant was centrifuged at 5500 rpm at 4° C. for 5 min, and resuspended with 1×Perm Buffer solution and centrifuged again to wash away unbound fluorescent antibody. The cells were resuspended with 200-300 μL PBS, the volume was adjusted, and the Ki67 expression level was analyzed with a flow cytometry.

FIG. 1 was a comparison chart of the proliferation ratios showing that a culture medium containing zoledronic acid was first used for stimulation and then four different cell culture mediums were used to conduct proliferation culture to the human Vγ9Vδ2T cells.

In FIG. 1, IL2 indicated what was used in the entire proliferation culture process was the culture medium obtained by adding IL2 based on the basic culture medium;

IL2+VC indicated what was used in the entire proliferation culture process was the culture medium obtained by adding IL2+VC based on the basic culture medium;

IL2+IL15 indicated what was used in the entire proliferation culture process was the culture medium obtained by adding IL2+IL15 based on the basic culture medium; and IL2+IL15+VC indicated what was used in the entire proliferation culture process was the culture medium obtained by adding IL2+IL15+VC based on the basic culture medium.

In the stage of stimulation and proliferation, the solutions of the above four culture mediums all used the basic culture medium added with ZOL (zoledronic acid) and IL-2 to stimulate the cells, and the amount of the components of each culture medium in FIG. 1 refers to the concentration as described in the portion of "Vγ9Vδ2T cell proliferation in vitro" of this example.

As shown in FIG. 1, after the above four culture mediums were respectively used for conducting proliferation culture to the human Vγ9Vδ2T cells, the obtained data showed that the cell proliferation efficiency of the culture medium (IL2 and IL2+VC), in which IL15 was not added, was relatively low, while the cell proliferation efficiency of the culture medium (IL2+IL15 and IL2+IL15+VC), in which IL15 was added, was relatively high, and thus, it could be seen that the adding of IL-15 could obviously improve the proliferation efficiency (rise of Ki67 protein expression) of the human Vγ9Vδ2T cells.

Figure 2:
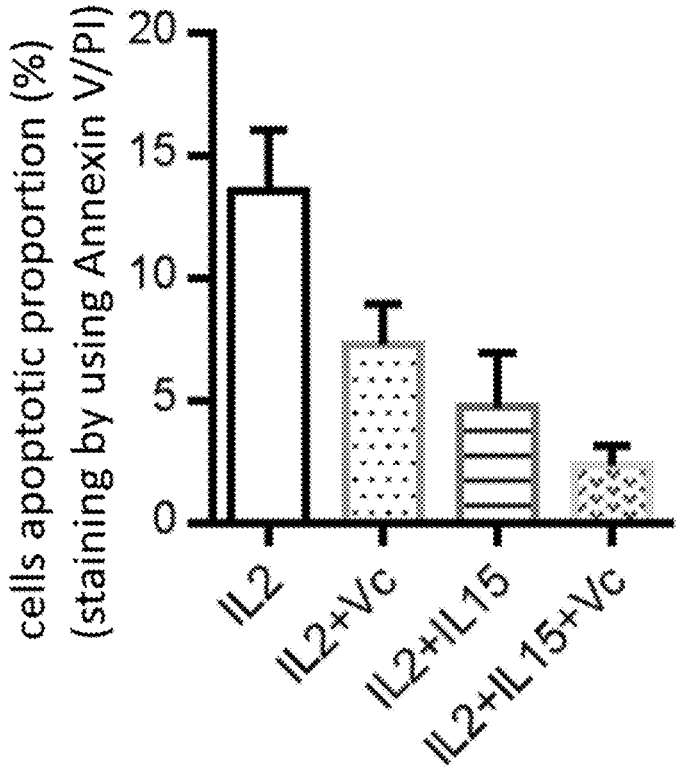
FIG. 2 is a comparison chart of the apoptosis ratios of the human Vγ9Vδ2T cells obtained by using four different culture mediums to conduct proliferation culture to the human Vγ9Vδ2T cells.

FIG. 2 was a comparison chart of the apoptosis ratio of the human Vγ9Vδ2 T cells obtained by using four different culture mediums to conduct proliferation culture to the human Vγ9Vδ2T cells, and IL2, IL2+VC, IL2+IL15, IL2+IL15+VC in FIG. 2 represented the same meanings with those in FIG. 1.

Based on FIG. 2, it could be seen that adding VC into the culture medium could obviously reduce the apoptosis ratio and apoptosis rate of cells, and in addition, the combination of IL-15 and VC could more significantly enhance the anti-apoptotic ability of cells.

Figure 3:
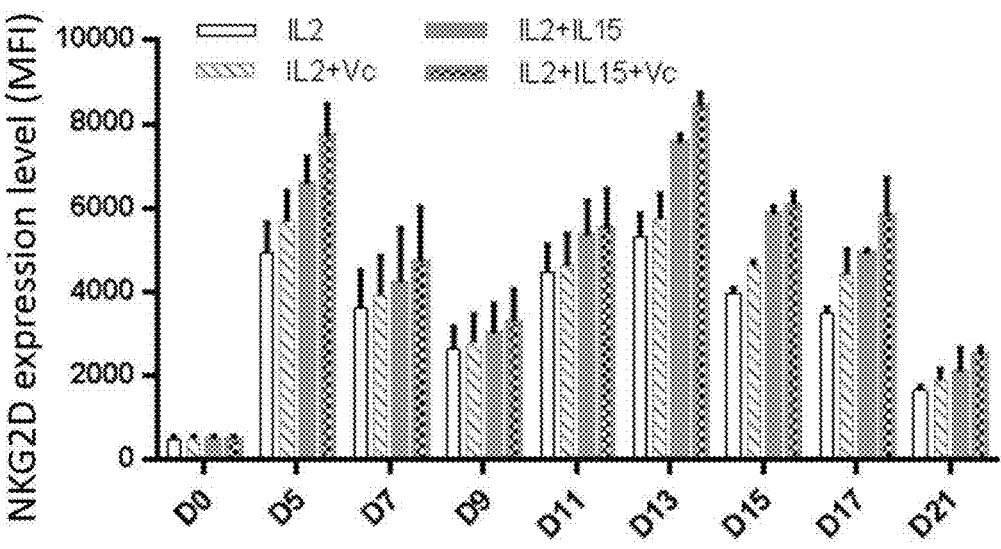
FIG. 3 is a comparison chart of the expression levels of critical killer molecule NKG2D of the human Vγ9Vδ2T cells obtained by using four different culture mediums to conduct proliferation culture to the human Vγ9Vδ2T cells.

FIG. 3 was a comparison chart of the expression levels of the critical killer molecule NKG2D of the human Vγ9Vδ2 T cells obtained by using four different culture mediums to conduct proliferation culture to the human Vγ9Vδ2T cells; and IL2, IL2+VC, IL2+IL15, IL2+IL15+VC in FIG. 3 represented the same meanings with those in FIG. 1 and FIG. 2.

Based on FIG. 3, it could be seen that the combination of IL-15 and vitamin C could make the critical killer molecule NKG2D of human Vγ9Vδ2T cells continuously maintain a high level of expression, and the critical killer molecule NKG2D could still maintain a high level of expression at the $21^{st}$ day of the culturing and after 21 days of culturing. In other words, the formula of the combination of IL-15 and VC (i.e., the technical solution of the present disclosure) could maintain a longer time of the high killing ability of human Vγ9Vδ2T cells.

Example 2: Anti-Tumor Effect of the Proliferated Vγ9Vδ2T Cells

Construction of Humanized Mouse Lung Cancer Model and Experimental Methods

1. Experimental Animals

Rag2$^{-/-}$γc$^{-/-}$ female mice aged 3-4 weeks were purchased from Taconic Company, which were of SPF grade. Immunodeficient mice used independently ventilated IVC cages. 5 mice were raised in each cage. Each isolator had independent NEPA air inlet and outlet and had 24-hour temperature and humidity control, and the feed and litter supply of the mice were vacuum-packed and sterilized by γ-radiation, and sterilized water was used as animal drinking water, and the animal raised in this environment was also packaged in a sterile environment; and the animals were transported in a biologically safe transportation box to ensure that the feeding and transportation were maintained in the same microbial state, so as to ensure and maintain the quality of the animals. The animal experiment was approved by the experimental animal ethics committee.

2. Method of Constructing Animal Models with Tumors

PBMC (huPBMC) were separated by Ficoll liquid density gradient centrifugation to construct humanized mouse models (huPBMCs humanized mice). The HLA type of constructing the humanized mouse-related PBMC was not consistent with the γδ T cells for reinfusion, and generally was HLA-A2+/−. It was convenient for distinguishing the γδ T cells for reinfusion and from the humanized mice themselves during subsequent detection.

Then, normal Rag2$^{-/-}$γc$^{-/-}$ mice aged 4-6 weeks were selected, after being irradiated with a sublethal dose of 300 cGay, 30×10$^6$ huPBMCs were injected intraperitoneally. After 4 weeks, the surviving humanized mice could be used for the construction of lung cancer models in the next step. After A549 cells growing adherently were digested, a cell suspension was prepared, and the concentration of A549 cells was adjusted to 1×10$^7$ cells/mL with phosphate buffered saline (PBS). The prepared cell suspension was inoculated into humanized mice by inguinal subcutaneous injection at a dose of 100 μL/mouse.

3. Use of Proliferated Vγ9Vδ2T Cells to Treat Animal Models

1) After 5-7 days of tumor formation, 5×10$^6$ γδ T cells cultured by IL-2, IL-2+VC, IL-2+IL-15, IL-2+Il-15+VC were injected into the humanized mouse model with lung cancer through the tail vein of the mouse every 3 days, and there were 5 mice in each group, and the dose is 100 μL/mouse. The PBS injection group was a control group of treatment. The γδ T cells cultured by IL-2, IL-2+VC, IL-2+IL-15 and IL-2+Il-15+VC were obtained by the method and steps described in the portion of "Vγ9Vδ2T cell proliferation in vitro" in embodiment 1, and IL2, IL2+VC, IL2+IL15 and IL2+IL15+VC represented the same meanings with those in FIG. 1 in embodiment 1.

2) After 3-4 times of treatment, they were observed for more than 60 days. The size of the tumor of the mice was measured using a vernier caliper twice a week, wherein the short diameter (A) and long diameter (B) of the tumor were used to calculate the tumor volume according to the formula:

$$V = \tfrac{1}{2} \times A^2 \times B.$$

3) After the reinfusion course of treatment was ended, the peripheral blood was drawn to detect the percentage and cell activity of the γδ T cells in the mice, and after the reinfusion was ended, the peripheral blood was drawn every two weeks to detect the percentage and cell activity of γδ T cells: NKG2D, PDI, CD107a, Fas and FasL.

4) Before the mice were sacrificed, the colonization situation of γδT cells in the mice was detected. GFP signal was detected at the same time, and the number and percentage of A549 tumor cells in peripheral blood were observed.

4. Experimental Result

The result of tumor treatment experiment was shown in FIGS. 4A, 4B, 4C, 5 and 6.

Figure 4A:
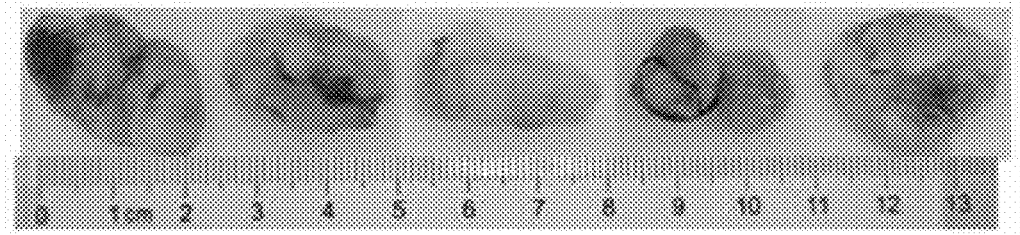
FIG. 4A is a schematic view of the size of tumor after a cell treatment to a humanized mouse with lung cancer using the human Vγ9Vδ2T cells obtained by a conventional proliferation method (IL-2)

FIG. 4A was a schematic view of the size of tumor after a cell treatment to a humanized mouse with lung cancer using the human Vγ9Vδ2T cells obtained by a conventional proliferation method (IL-2).

The conventional proliferation method (the second type of proliferating technology) was always to add IL2 into the basic culture medium for culturing and to add ZOL for stimulating proliferation in the early stage of the culturing.

Figure 4B:
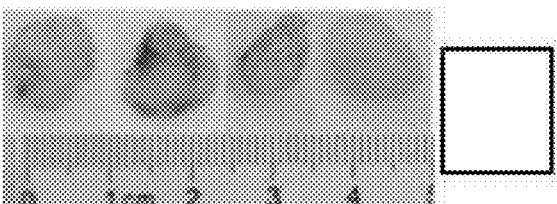
FIG. 4B is a schematic view of the size of tumor after a cell treatment to a humanized mouse with lung cancer using the human Vγ9Vδ2T cells obtained by a proliferation method (IL2+IL15+VC) of the present disclosure.

FIG. 4B was a schematic view of the size of tumor after a cell treatment to a humanized mouse with lung cancer using the human Vγ9Vδ2T cells obtained by the proliferation method (IL2+IL15+VC) of the present disclosure.

Figure 4C:
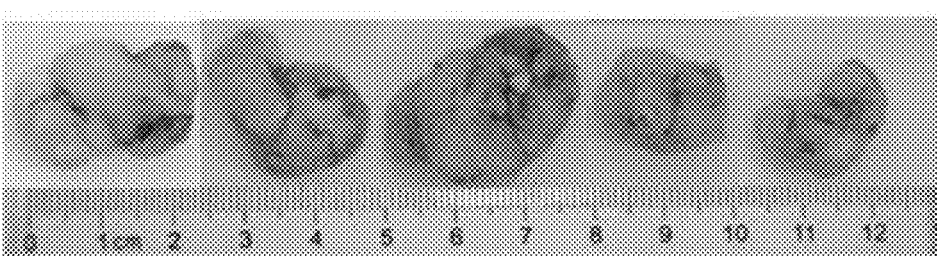
FIG. 4C is a schematic view of the size of tumor of a humanized mouse with lung cancer in the case of not being treated.

FIG. 4C was a schematic view of the size of tumor of the humanized mouse with lung cancer in the case of not being treated.

The humanized mice with lung cancer used in the experiments as illustrated in FIGS. 4A, 4B and 4C had the same tumor type and substantively the same tumor volume, and growing time of the tumor as illustrated in FIGS. 4A, 4B and 4C were the same.

Through the comparison of FIGS. 4A, 4B and 4C, it could be seen that after the human Vγ9Vδ2T cells obtained by the proliferation method of the present disclosure were used to perform cell treatment on the humanized mice with lung cancer, compared with the human Vγ9Vδ2T cells obtained by a conventional proliferation method, the human Vγ9Vδ2T cells proliferated by the present disclosure could more effectively suppress the growth of lung cancer cells (the size of the tumor was significantly reduced), and could significantly improve the survival rate of humanized mice with lung cancer. On the $42^{nd}$ day, the humanized mice with lung cancer that were treated with human Vγ9Vδ2T cells obtained by a conventional proliferation method and the untreated humanized lung cancer mice all died, however, the humanized mice with lung cancer that were treated with human Vγ9Vδ2T cells obtained by the proliferation method of the present disclosure all survived with a survival rate of 100%, and the tumor in one mouse completely disappeared (shown in the block of FIG. 4B).

Figure 5:
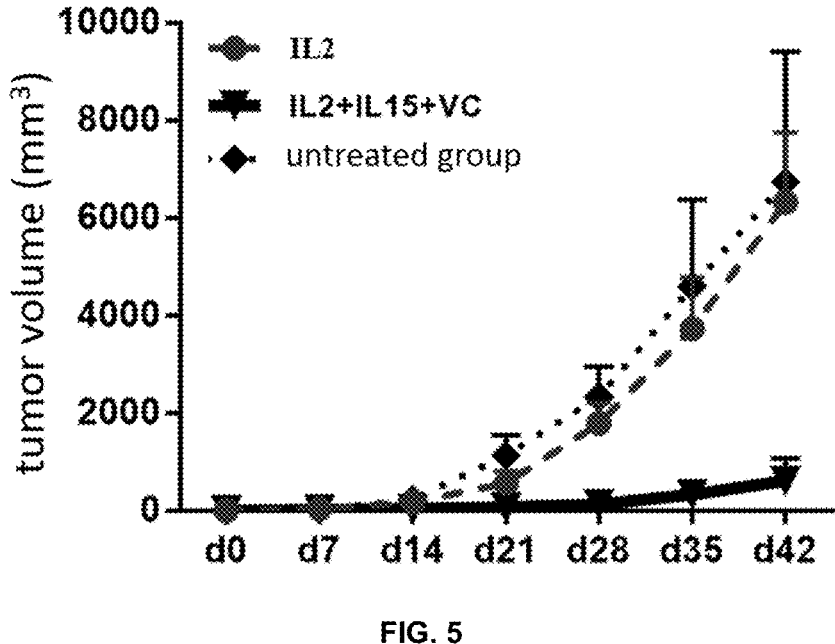
FIG. 5 is a schematic view of the variations of the volume of the tumor of humanized mouse with lung cancer under different treating conditions.

FIG. 5 was a schematic view of the variations of the volume of the tumor of the humanized mice with lung cancer under different treating conditions, and FIG. 5 respectively illustrated the volume changes of the tumor of the humanized mice with lung cancer when the humanized mice with lung cancer were treated with the human Vγ9Vδ2T cells obtained by the conventional proliferation method (IL2) and with the human Vγ9Vδ2T cells obtained by the proliferation method (IL2+IL15+VC) of the present disclosure, and were not treated.

It could be seen that with the increase of time, the volumes of tumors of the humanized mice with lung cancer which were treated with human Vγ9Vδ2T cells obtained by the conventional proliferation method (IL2) and which were not treated increased continuously, and the tumor volumes increased very quickly in the later stage, however, the tumor volume of humanized mice with lung cancer treated with the human Vγ9Vδ2T cells obtained by the proliferation method (IL2+IL15+VC) of the present disclosure increased very slowly, in other words, compared with the human Vγ9Vδ2T cells obtained by the conventional proliferation method (IL2), the human Vγ9Vδ2T cells obtained by the proliferation method (IL2+IL15+VC) of the present disclosure had a stronger suppressing effect on tumor growth in vivo, and rendered smaller tumor volumes.

Figure 6:
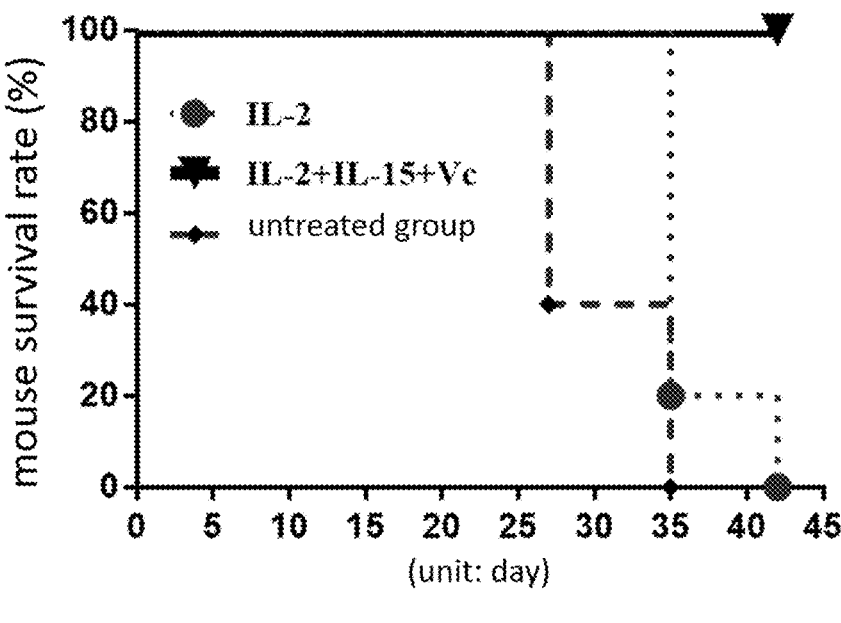
FIG. 6 is a schematic view of the variations of the survival rate of humanized mouse with lung cancer under different treating conditions.

FIG. 6 was a schematic view of the variations of the survival rates of the humanized mice with lung cancer under different treating conditions, and FIG. 6 respectively illus-trated the variations of the survival rates of the humanized mice with lung cancer which were treated with the human Vγ9Vδ2T cells obtained by the conventional proliferation method (IL2) and with the human Vγ9Vδ2T cells obtained by the proliferation method (IL2+IL15+VC) of the present disclosure, and which were not treated.

It could be seen that with the increase of time, the survival rates of the humanized mice with lung cancer which were treated with human Vγ9Vδ2T cells obtained by the conventional proliferation method (IL2) and which were not treated reduced very quickly, however, the survival rate of the humanized mice with lung cancer treated with the human Vγ9Vδ2T cells obtained by the proliferation method (IL2+IL15+VC) of the present disclosure was always 100%, in other words, the human Vγ9Vδ2T cells obtained by the proliferation method (IL2+IL15+VC) of the present disclosure could significantly improve the survival rate of the humanized mouse with lung cancer.

Example 3

The example 1 provided a second culture medium, which comprised a RPMI-1640 culture medium, and interleukin-2, interleukin-15 and vitamin C added in the RPMI-1640 culture medium.

In the above, in the second culture medium, the concentration of the interleukin-2 was 300 ng/ml, the concentration of the interleukin-15 was 500 ng/ml, and the concentration of the vitamin C was 100 mM.

Example 4

The example 2 provided a second culture medium, which comprised a RPMI-1640 culture medium, and interleukin-2, interleukin-15 and vitamin C added in the RPMI-1640 culture medium.

In the above, in the second culture medium, the concentration of the interleukin-2 was 500 ng/ml, the concentration of the interleukin-15 was 700 ng/ml, and the concentration of the vitamin C was 300 mM.

Example 5

The example 3 provided a first culture medium, which comprised the second culture medium as mentioned in the example 1 and zoledronic acid.

In the above, in the first culture medium, the concentration of the zoledronic acid was 300 μM.

Example 6

The example 4 provided a first culture medium, which comprised the second culture medium as mentioned in the example 2 and zoledronic acid.

In the above, in the first culture medium, the concentration of the zoledronic acid was 500 μM.

It is difficult to describe all the numerical ranges of the process parameters involved in the present disclosure in the above-mentioned embodiments, but those skilled in the art can fully imagine that any value falling within the above-mentioned value range can perform the present disclosure, and certainly the present disclosure contains any combination of specific values of several numerical ranges. Here, for the sake of space, the embodiments providing specific values within one or more numerical ranges are omitted, while this should not be regarded as insufficient disclosure of the technical solutions of the present disclosure.

The applicant declares that the above-mentioned embodiments in the present disclosure are used to describe the specific process equipment and the process flow of the present disclosure, but the present disclosure are not limited to the above process equipment and process flow, that is, it does not mean that the present disclosure can only be implemented depending on the above specific process equipment and process flow. A person skilled in the art should understand that any improvement to the present disclosure, and equivalent substitutions to each material of the product of the present disclosure, and the addition, the selection of the specific methods of auxiliary components and the like all fall within the scope of the present disclosure.

INDUSTRIAL APPLICABILITY

Compared with a conventional proliferation method (the second type of proliferation technology), the human Vγ9Vδ2T cells obtained by the proliferation method of the present disclosure has a higher proliferation efficiency and a higher cell purity, and the proliferation method of the present disclosure obviously shortens the proliferation culture period of the human Vγ9Vδ2T cells. Compared with the human Vγ9Vδ2T cells obtained by the conventional proliferation method (the second type of proliferating technology), the human Vγ9Vδ2T cells obtained by the proliferation method of the present disclosure have stronger killing and suppressing abilities to tumor. The human Vγ9Vδ2T cells obtained by the proliferation method of the present disclosure have a stronger anti-apoptotic ability and a longer survival time.

What is claimed is:

1. A method for selectively proliferating Vγ9Vδ2T cells, comprising:
    step A, culturing a composition containing the T cells, by using a first culture medium which is able to stimulate T cells, so as to stimulate the T cells, wherein the first culture medium comprises interleukin-2 and phosphonic acid compounds, and the phosphonic acid compounds are selected from the group consisting of zoledronic acid, etidronic acid, ibandronic acid, pamidronic acid, alendronic acid, risedronic acid, minodronic acid and combinations thereof; and
    step B, using a second culture medium to culture the stimulated T cells, wherein the second culture medium contains interleukin-2, interleukin-15, and vitamin C or a derivative of vitamin C, thereby selectively proliferating the Vγ9Vδ2T cells.

2. The method according to claim 1, wherein the first culture medium comprises interleukin-15, and vitamin C or a derivative of vitamin C.

3. The method according to claim 1, wherein the derivative of vitamin C is selected from the group consisting of vitamin C ethyl ether, vitamin C palmitate, vitamin C glucoside, vitamin C magnesium phosphate and vitamin C sodium phosphate and combinations thereof.

4. The method according to claim 1, wherein in the second culture medium, a concentration of the interleukin-15 is 1-1000 ng/ml.

5. The method according to claim 1, wherein in the second culture medium, a concentration of the vitamin C or the derivative of vitamin C is 10 μM-800 mM.

6. The method according to claim 1, wherein in the second culture medium, a concentration of the interleukin-2 is 1-1000 ng/ml.

7. The method according to claim 1, wherein the composition containing the T cells comprises peripheral blood mononuclear cells extracted from peripheral blood of human body.

8. The method according to claim 1, wherein the step A comprises culturing the composition containing the T cells for 60-100 hours.

9. The method according to claim 1, wherein the second culture medium further comprises a basic culture medium, wherein the basic culture medium is selected from the group consisting of Roswell Park Memorial Institute Medium 1640, Dulbecco's Modified Eagle Medium, Minimum Essential Medium, Roswell Park Memorial Institute Medium, Opti-Minimum Essential Medium and combinations thereof.

10. A method for treating a malignant disease, comprising:
    (1) extracting peripheral blood mononuclear cells from peripheral blood of a subject in need;
    (2) proliferating the peripheral blood mononuclear cells through the method according to claim 1; and
    (3) administering proliferated product to the subject in need,
    wherein the peripheral blood mononuclear cells are used as the composition containing the T cells, and the malignant disease is lung cancer.

* * * * *